United States Patent [19]

Maier et al.

[11] Patent Number: 5,164,436
[45] Date of Patent: Nov. 17, 1992

[54] WAXY COMPOUNDS OF AROMATIC ALCOHOLS, THEIR PREPARATION AND THEIR USE

[75] Inventors: Karl Maier, Augsburg; Gerd Hohner, Gersthofen; Jan-Peter Piesold, Augsburg, all of Fed. Rep. of Germany

[73] Assignee: Hoechst Aktiengesellschaft, Frankfurt, Fed. Rep. of Germany

[21] Appl. No.: 730,571

[22] Filed: Jul. 15, 1991

Related U.S. Application Data

[63] Continuation of Ser. No. 432,615, Nov. 7, 1989, abandoned, which is a continuation of Ser. No. 195,088, May 17, 1988, abandoned.

[30] Foreign Application Priority Data

Nov. 23, 1988 [DE] Fed. Rep. of Germany ....... 3716723

[51] Int. Cl.$^5$ .................. C07C 69/26; C07C 69/28; C07C 69/30; C07C 67/08
[52] U.S. Cl. ................................. 524/290; 524/277; 524/278; 524/291
[58] Field of Search ............... 524/277, 278, 291, 290

[56] References Cited

U.S. PATENT DOCUMENTS

| | | | |
|---|---|---|---|
| 3,442,837 | 5/1969 | Brotz et al. | 524/278 |
| 3,479,309 | 11/1969 | Hecker et al. | 524/400 |
| 3,943,165 | 3/1976 | Lamberti | 524/290 |
| 4,097,435 | 6/1978 | Rawlings et al. | 524/277 |
| 4,143,105 | 3/1979 | Hertschel et al. | 428/18 |
| 4,207,270 | 6/1980 | Mayer et al. | 524/119 |
| 4,508,876 | 4/1985 | Takaki et al. | 525/310 |
| 4,582,783 | 4/1986 | Nittel et al. | 430/527 |

FOREIGN PATENT DOCUMENTS 95943 8/1981 Japan.
1528193 10/1978 United Kingdom.

*Primary Examiner*—Paul R. Michl
*Assistant Examiner*—Andrew E. C. Merriam
*Attorney, Agent, or Firm*—Connolly and Hutz

[57] ABSTRACT

Waxy esters of aromatic alcohols with long-chain carboxylic acids give lubricants and release agents for highly transparent thermoplastics which reduce the transparency of these plastics to a far lesser degree than the previously customary montan wax esters of aliphatic alcohols.

12 Claims, No Drawings

WAXY COMPOUNDS OF AROMATIC ALCOHOLS, THEIR PREPARATION AND THEIR USE

This application is a continuation of application Ser. No. 07/432,615, filed Nov. 7, 1989, now abandoned, which is a continuation of application Ser. No. 07/195,088, filed May 17, 1988, now abandoned.

DESCRIPTION

The invention relates to wax esters of aromatic alcohols, their preparation and their use as lubricants and release agents for thermoplastics.

The use of lubricants and release agents in the processing of polyvinyl chloride, polystyrene, polyesters and other thermoplastics has already been known for a long time and is generally familiar. Fatty acid derivatives, long-chain alcohols and montan waxes are preferably used as such compounds. Although the fatty acid derivatives, such as, for example, N,N'-ethylene-bis-stearamide, improve the flow properties of the polymer melt and give highly transparent end products, their volatility and the odor they develop is troublesome at the high processing temperatures which frequently arise. Although the previously customary montan waxes do not have these troublesome properties, the amount in which they can be added is limited since they can cause clouding.

Waxy esters of phenols and aromatic, aliphatic or cycloaliphatic alcohols with long-chain carboxylic acids are known and are said to be used as lubricants in processing of PVC (compare EP-PS 11,325). Nevertheless, a large number of phenols and alcohols are mentioned in this publication, and the carboxylic acids should be branched-chain to the extent of at least 40% by weight.

The use of a compound of the formula

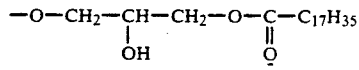

as a lubricant for processing PVC has furthermore been described (compare Japanese Published Specification 76, 147,545). The compound is said to improve the processability of PVC. Whether this also applies to the transparency of the molding is not disclosed.

There was thus the object of discovering lubricants and release agents which have the positive properties of montan waxes without their tendency to cause clouding.

The invention therefore relates to the waxy compounds described in the claims, a process for their preparation and their use as lubricants and release agents for thermoplastics.

The wax esters according to the invention are compounds of the formula (I)

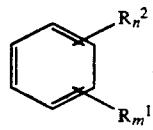 (I)

and are formed by reaction of compounds of the formula (II)

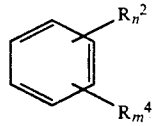 (II)

or of the formula (IV)

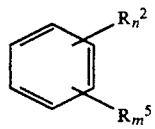 (IV)

with carboxylic acids of the formula (III)

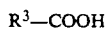

$R^3$—COOH (III).

In these formulae,
$R^1$ denotes the group

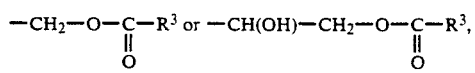

$R^2$ denotes an alkyl radical with 1 to 4 carbon atoms or halogen, preferably an alkyl radical with 1 to 2 carbon atoms, or chlorine,
$R^3$ denotes an unbranched alkyl radical with 20 to 36 carbon atoms, preferably with 26 to 32 carbon atoms,
$R^4$ denotes the group —$CH_2OH$ or —$CH(OH)$—$CH_2OH$, preferably —$CH_2OH$,
$R^5$ denotes the group

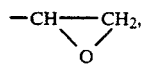

m denotes 1, 2 or 3, preferably 1 or 2, and
n denotes zero to (6-m), preferably zero to 3.

Examples of suitable starting compounds of the formula (II) are benzyl alcohol, o-, m- and p-tolylcarbinol, chlorobenzyl alcohol, bromobenzyl alcohol, 2,4-dimethylbenzyl alcohol, 3,5-dimethylbenzyl alcohol, 2,3,5-cumobenzyl alcohol, 3,4,5-trimethylbenzyl alcohol, p-cuminyl alcohol, 1,2-phthalyl alcohol, 1,3-bis(hydroxymethyl)benzene (=m-xylylene alcohol), 1,4-bis(-hydroxymethyl)benzene (=p-xylylene alcohol), pseudocumenyl glycol, mesitylene glycol and mesitylene glycerol.

A suitable starting compound of the formula (IV) is, for example, styrene oxide.

Suitable carboxylic acids of the formula (III) are, for example, arachic acid, behenic acid, tetracosanoic acid, cerotic acid, montanic acid and melissic acid, preferably cerotic acid, montanic acid and melissic acid, in particular technical grade montanic acid, which is essentially a mixture of $C_{18}$-$C_{36}$-carboxylic acids with a predominant content of $C_{26}$-$C_{32}$-carboxylic acids and is obtained by oxidative bleaching of crude montan wax.

The reaction of the alcohol of the formula (II) with the carboxylic acid of the formula (III) can be carried out in an inert solvent. Suitable solvents are aliphatic and aromatic hydrocarbons, preferably aromatic hydrocarbons, such as, for example, toluene or xylene.

Preferably, however, the reaction is carried out in the absence of a solvent by taking the carboxylic acid in molten form and introducing the alcohol into the melt. The water of reaction formed is distilled off. The progress of the reaction is monitored by continuous determination of the acid number. The reaction is carried out in the presence of a catalyst, such as, for example, sulfuric acid, toluene- or naphthalenesulfonic acid or salts of tin or zinc. Sulfuric acid is preferably used. The alcohol and carboxylic acid are used in a molar ratio of 2.0:1 to 0.1:1, 1.0:1 to 0.5:1. The reaction temperature is in the range from 50° to 200° C., preferably 90° to 160° C. The carboxylic acid can be esterified either completely or partly up to a desired residual acid number of the reaction mixture. Alcohol present in excess can be separated off after the reaction by distillation, extraction or a similar process.

The compounds of the formula (I) where $R^1 =$

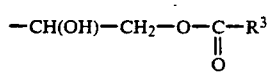

can also be prepared by reacting an epoxide of the formula (IV) with a carboxylic acid of the formula (III) in the presence of a catalyst, for example chromium(III) salts, aliphatic or aromatic amines or aluminum oxide, preferably aliphatic tertiary amines, such as trimethyl- or triethylamine. The procedure is otherwise analogous to that for the reaction between an alcohol and a carboxylic acid.

After being formed, the esters according to the invention can be treated with alkali metal or alkaline earth metal bases in order to neutralize excess carboxylic acid or to form a certain proportion of metal soaps by partial saponification. Calcium hydroxide is preferably used for the partial saponification.

The compounds of the formula (I) according to the invention are white to yellowish waxes with an acid number in the range from 0 to 190, a saponification number in the range from 90 to 200 and a drop point from 60° to 120° C.

They have a uniformly good lubricating and releasing effect compared with the previously customary montan wax esters of aliphatic alcohols, but result in a significantly better transparency. Because of their very good transparency properties, the wax esters according to the invention are preferably used for processing highly transparent thermoplastics.

Such highly transparent thermoplastics are obtained, for example, by polymerization of vinyl chloride, vinylidene chloride, ethylvinyl acetate, acrylonitrile, acrylic acid (esters), methacrylic acid (esters), styrene, α-methylstyrene, p-methylstyrene or mixtures of these monomers. Other highly transparent thermoplastics for processing of which the use of the ester waxes according to the invention is particularly appropriate are polycondensation products, such as, for example, polycarbonate, polyethylene terephthalate, polybutylene terephthalate polyphenylene oxide, polysulfones, polyether-sulfones and polyaryl ethers.

The wax esters according to the invention can furthermore also be used in the processing of polymer mixtures, so-called polymer blends.

Although the particular advantage of the ester waxes according to the invention lies in the field of highly transparent thermoplastic molding materials, they can of course also be used for non-transparent molding materials. The content of wax in the molding material is 0.01 to 5% by weight, preferably 0.05 to 2.5% by weight and in particular 0.5 to 1% by weight.

The molding materials can additionally also contain other additives, such as, for example, antioxidants, for example alkylated monophenols, alkylated hydroquinones, hydroxylated thiodiphenyl ethers, alkylidenebisphenols, benzyl compounds, acylaminophenols, esters of β-(5-tert.- butyl-4-hydroxy-3-methylphenyl)-propionic acid, amides of β-(3,5-di-tert.-butyl-4-hydroxyphenyl)-propionic acid, UV absorbers and light stabilizers, for example 2-(2'-hydroxyphenyl)-benzotriazoles, 2-hydroxybenzophenones, esters of optionally substituted benzoic acids, acrylates, nickel compounds, sterically hindered amines, oxalic acid diamides, metal deactivators, phosphates and phosphonites, peroxide-destroying compounds, basic costabilizers, nucleating agents, fillers and reinforcing agents, plasticizers, optical brighteners, flameproofing agents, antistatics, propellants and other lubricants.

The wax esters are incorporated into he molding materials in a known manner, for example by means of mixers, extruders, roll mills or kneaders.

The following examples are intended to illustrate the invention. The amounts stated relate to the weight.

EXAMPLE 1

500 g of technical grade montan wax acid (acid number 138, 1.23 mole) were melted in a Witt pot (with a stirrer, thermometer, distillation bridge and $N_2$ blanketing), and 131.6 g (1.22 mole) of benzyl alcohol and 0.5 ml of $H_2SO_4$ (44% strength) were added at 120° C. The mixture was stirred until the acid number had fallen to about 25 mg of KOH/g (about 3 hours), a mixture of water of reaction and benzyl alcohol distilling over. The batch was then neutralized with aqueous sodium hydroxide solution against thymol blue, bleached with 5 ml of $H_2O_2$ (30% strength), freed from volatile constituents under reduced pressure and subjected to pressure filtration. A pale wax was obtained.

| Acid number | 26 |
|---|---|
| Saponification number | 159 |
| Drop point | 76° C. |

EXAMPLE 2

100 g of technical grade montan wax acid (acid number 110, 0.20 mole) were melted in a 250 ml three-necked flask (with a stirrer, thermometer and dropping funnel). 0.2 g of triethylamine was added at an internal temperature of 140° C., and 23.2 g (0.19 mole) of styrene oxide were then added dropwise in the course of 30 minutes. After about 2 hours, the acid number remained constant at 18. Volatile constituents were removed by applying reduced pressure. A pale wax was obtained.

| Acid number | 17 |
|---|---|
| Saponification number | 124 |
| Drop point | 81° C. |

In the examples below, the terms have the following meanings:
Wax 1: montanic acid ester of ethylene glycol,
Wax 2: montanic acid ester of 1,3-butanediol, partly saponified (1.4% by weight of Ca),
Wax 3: montanic acid ester of glycerol, Wax 4: montanic acid ester of benzyl alcohol,
Wax 5: montanic acid ester of benzyl alcohol, partly saponified (1.4% by weight of Ca),
Wax 6: montanic acid ester of β-hydroxy-β-phenylethanol, partly saponified (1.4% by weight of Ca),
Wax 7: montanic acid ester of 1,4-bis(hydroxymethyl)-benzene, partly saponified (1.4% by weight of Ca).

Waxes 1, 2 and 3 are commercially available and are used for comparison, and waxes 4 to 7 are according to the invention.

EXAMPLE 3

100.0 parts of S-PVC (K value 60)
1.0 part of processing aid based on PMMA
1.5 parts of dioctyltin thioglycolate
0.3 part of glycerol monostearate and
0.6 part of test product
were plasticized on a test roll mill at a temperature of 190° C. and the mixture was then pressed to sheets 0.5 or 2.0 mm thick. These were tested for their transparency.

| Wax | Transparency/0.5 mm | Transparency/2.0 mm |
|---|---|---|
| 1 | 68.2 | 41.4 |
| 2 | 83.4 | 71.6 |
| 3 | 77.1 | 54.4 |
| 5 | 88.8 | 84.4 |
| 6 | 87.1 | 82.5 |
| 7 | 84.6 | 71.0 |

EXAMPLE 4

As Example 1, with 5.0 parts of an impact strength agent.

The suitability of the lubricant was tested in a Brabender kneader (32 g weighed out; 40 rpm; 160° C.; 2 kg load) and on a test roll mill (190° C.; 15/20 rpm).

| | Kneader | | | Roll Mill | |
|---|---|---|---|---|---|
| Wax | Plasticizing time min | Maximum torque Nm | Constant torque Nm | Tack-free time min | Final Stability |
| 1 | 1.8 | 36.0 | 23.8 | 21 | 40 |
| 2 | 1.8 | 33.0 | 23.2 | 30 | 40 |
| 5 | 1.2 | 37.0 | 24.0 | 21 | 40 |
| 6 | 1.3 | 36.1 | 23.7 | 27 | 43 |
| 7 | 1.0 | 35.5 | 22.8 | 27 | 39 |

EXAMPLE 5

A polyethylene terephthalate with a specific viscosity of 1060 (SV value) was mixed with 0.3% by weight of various waxes. 1 mm sheets of this mixture were injection-molded on an injection molding machine (material temperature 280° C., mold temperature 30° C.).

| Wax | Transparency |
|---|---|
| none | 86.6 |
| 1 | 79.0 |
| 2 | 78.2 |
| 4 | 85.0 |

EXAMPLE 6

Polystyrene (MFI 200/5: 25 g/10 minutes; DIN 53735) was mixed with in each case 1% of wax in a Brabender kneader at 180° C. for 10 minutes. The melt was then pressed to sheets 2 mm thick, which were investigated for their transparency.

| Wax | Kneading resistance | Transparency | Remarks |
|---|---|---|---|
| none | 8.8 Nm | 83.7% | sticks in the Brabender |
| 1 | 7.8 Nm | 53.7% | smearing |
| 4 | 8.5 Nm | 83.8% | no sticking |
| 6 | 8.5 Nm | 82.4% | no sticking |
| 7 | | 64.5% | no sticking |

HKV measurements confirmed the good lubricant properties of the new montan waxes. For these, the sheets described above were granulated, and the measurements were carried out at 170° C. with a 1 mm die (L/D=30).

| Wax 1% | Output in g/10 minutes | | | |
|---|---|---|---|---|
| | 115 | 170 | 225 | 280 |
| none | 3.1 | 8.7 | 20.2 | 38.8 |
| 1 | 4.0 | 11.3 | 28.6 | 52.7 |
| 4 | 3.9 | 11.2 | 27.7 | 49.9 |
| 6 | 4.0 | 12.3 | 30.3 | 51.2 |
| 7 | 3.6 | 10.4 | 25.1 | — |

We claim:
1. A process for molding a polymer which can be processed in a molding device as a thermoplastic and for facilitating the release of the resulting molded article from the molding device, which comprises the steps of:
adding to said polymer a waxy release agent comprising a compound of the formula (I)

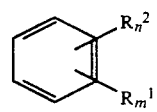

in which $R^1$ is the group

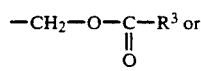

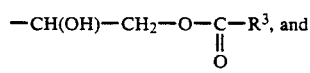

$R^2$ is an alkyl radical with 1–4 carbon atoms or halogen,
$R^3$ is an unbranched alkyl radical with 20–36 carbon atoms,
m is 1, 2 or 3 and n is 0 to (6-m);
molding the polymer in the molding device; and recovering the resulting molded article from the molding device, and
in which the polymer is a polystyrene, poly-α-methyl-styrene, poly-p-methylstyrene, poly(meth)acrylate, polyether, polycarbonate, polyamide, polyether-ketone, polysulfone, polyethylene terephthalate or polyether-sulfone or a mixture of these polymers.

2. The process as claimed in claim 1, wherein the polymer is transparent prior to the addition of the waxy release agent, and wherein the thermoplastic molding material which results after the addition of the waxy release agent to the polymer is transparent also.

3. A thermoplastic molding material consisting essentially of a polymer which can be processed as a thermoplastic and 0.01–5.0%, based on the molding material, of a waxy compound of the formula (I)

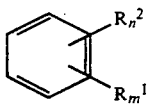
(I)

in which $R^1$ is the group

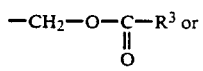

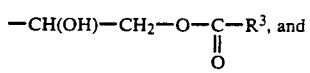

$R^2$ is an alkyl radical with 1–4 carbon atoms or halogen, $R^3$ is an unbranched alkyl radical with 20–36 carbon atoms, m is 1, 2 or 3 and n is 0 to (6-m) and, in which the polymer is a polystyrene, poly-α-methyl-styrene, poly-p-methylstyrene, poly(meth)acrylate, polyether, polycarbonate, polyamide, polyether-ketone, polysulfone, polyethylene terephthalate or polyether-sulfone or a mixture of these polymers.

4. A thermoplastic molding material as claimed in claim 3, wherein the waxy compound has the formula

where $R^1$ is the group —$CH_2$—$OCOR^3$ or —CH(OH)$CH_2OCOR^3$, and $R^3$ is an unbranched alkyl radical with 20–36 carbon atoms.

5. The process as claimed in claim 1, wherein the waxy release agent is a compound of formula I in which:

$R^1$ is the group —$CH_2OCOR^3$, n is zero, and m is 1, and the polymer is a polystyrene.

6. The process as claimed in claim 1, wherein the polymer is a polystyrene.

7. The process as claimed in claim 1, wherein the polymer is or a polystyrene and the waxy release agent is the benzyl ester of montanoic acid.

8. A thermoplastic molding material as claimed in claim 3, wherein the polymer is a polystyrene.

9. A thermoplastic molding material as claimed in claim 4, wherein the molding material is transparent, and the polymer is a polystyrene.

10. A thermoplastic molding material consisting essentially of a polymer which can be processed as a thermoplastic and 0.01–5.0%, based on the molding material of a waxy compound, wherein the waxy compound is benzyl ester of montanoic acid and the polymer is a polystyrene and said molding material is transparent.

11. A thermoplastic molding material as claimed in claim 3, wherein the polymer is a polyethylene terephthalate.

12. A thermoplastic molding material as claimed in claim 3, wherein the polymer is a polycarbonate.

* * * * *